United States Patent [19]
Liberman et al.

[11] Patent Number: 6,097,205
[45] Date of Patent: Aug. 1, 2000

[54] METHOD AND APPARATUS FOR CHARACTERIZING A SPECIMEN OF SEMICONDUCTOR MATERIAL

[75] Inventors: Sergey Liberman, Bedford, Mass.;
Peter L. Domenicali, Montpelier, Vt.;
Alan H. Field, Topsfield, Mass.;
Charles M. Kohn, Needham, Mass.;
Glendon P. Marston, Manchester, Mass.

[73] Assignee: Semitest, Inc., Billerica, Mass.

[21] Appl. No.: 08/941,710

[22] Filed: Sep. 30, 1997

Related U.S. Application Data

[63] Continuation-in-part of application No. 08/873,410, Jun. 12, 1997, Pat. No. 6,034,535
[60] Provisional application No. 60/038,003, Feb. 14, 1997.
[51] Int. Cl.[7] .......................... G01R 31/28; G01R 31/26
[52] U.S. Cl. .................. 324/765; 324/662; 324/719; 324/752; 324/766
[58] Field of Search ............................. 324/765, 766, 324/767, 719, 750, 752, 662; 257/335, 336, 48

[56] References Cited

U.S. PATENT DOCUMENTS

| | | | |
|---|---|---|---|
| 3,857,095 | 12/1974 | Mitchie et al. | 324/662 |
| 4,112,455 | 9/1978 | Seliger et al. | 257/335 |
| 4,115,736 | 9/1978 | Tracy | 324/760 |
| 4,422,089 | 12/1983 | Vaes et al. | 257/336 |
| 4,812,756 | 3/1989 | Curtis et al. | 324/750 |
| 5,091,691 | 2/1992 | Kameiniecki et al. | 324/765 |
| 5,166,765 | 11/1992 | Lee et al. | 257/345 |
| 5,216,362 | 6/1993 | Verkuil | 324/767 |
| 5,359,221 | 10/1994 | Miyamoto et al. | 257/335 |
| 5,442,297 | 8/1995 | Verkuil | 324/766 |
| 5,543,654 | 8/1996 | Dennen | 257/327 |
| 5,742,167 | 4/1998 | Haynes | 324/662 |

*Primary Examiner*—Ernest Karlsen
*Attorney, Agent, or Firm*—Kriegsman & Kriegsman

[57] ABSTRACT

A method and apparatus are provided for determining the doping concentration profile of a specimen of semiconductor material. The specimen is positioned between a pair of electrodes, the specimen being disposed on one of the electrodes and being spaced form the other electrode by a nonconductive medium. In one implementation of the invention the nonconductive medium is air. A region of the surface of the specimen is illuminated with a beam of light of wavelengths shorter than that corresponding to the energy gap of the semiconductor material and which is intensity modulated at a predetermined frequency. A variable DC bias voltage is applied between the pair of electrodes, the variable DC bias voltage varying between that corresponding to accumulation and that corresponding to deep depletion for the specimen. The intensity of the light beam is low enough and the speed at which the DC bias voltage is varied is fast enough such that no inversion layer is formed at the surface of the specimen. A signal is also provided corresponding to the total capacitance between the two electrodes during the DC bias voltage sweep. A signal is provided representing the ac photocurrent induced at the region of the specimen illuminated by the light beam. The intensity of the light beam and frequency of modulation of the light beam are selected such that the ac photocurrent is nearly proportional to the intensity of the light beam. The doping concentration profile is then determined using the ac photocurrent, the total capacitance and the DC bias voltage. The apparatus includes a sensor assembly having a sensor tip which is mounted on an air bearing assembly. The air bearing assembly is suspended from a housing by a pair of bellows. In use, air is supplied to the air bearing assembly through the bellows causing the bellows to expand, lowering the sensor tip until the air bearing action stops the expansion. In another implementation of the invention, a light beam is not employed and the doping concentration profile is determined using the total capacitance, the capacitance of air, the DC bias voltage and the area of the electrode spaced from the specimen information.

33 Claims, 7 Drawing Sheets

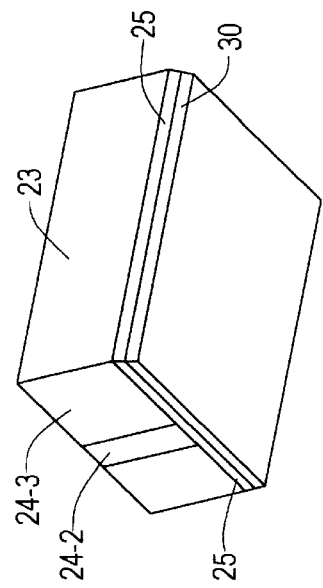
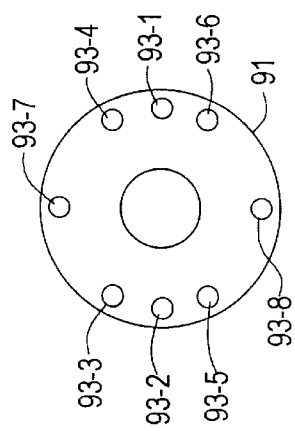
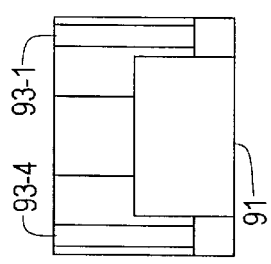
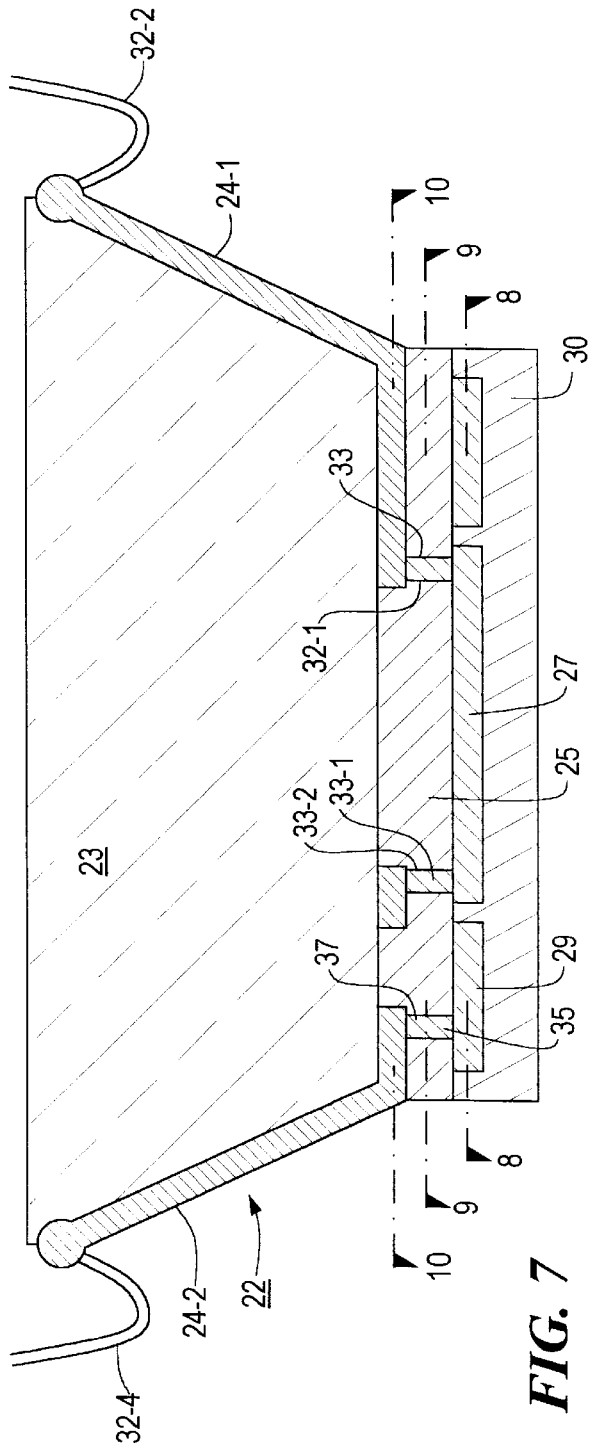

METHOD AND APPARATUS FOR CHARACTERIZING A SPECIMEN OF SEMICONDUCTOR MATERIAL

CROSS-REFERENCE TO RELATED APPLICATIONS

This application is a continuation-in-part of U.S. patent application Ser. No. 08/873,410 filed on Jun. 12, 1997, now U.S. Pat. No. 6,034,535, and is claiming the priority of provisional application Ser. No. 60/038,003, filed on Feb. 14, 1997.

BACKGROUND OF THE INVENTION

1. Field of the Invention

The present invention relates to a method and apparatus for characterizing a specimen of semiconductor material and, more particularly, to a method and apparatus determining parameters such as the doping concentration profile of a specimen of semiconductor material.

2. Description of Prior Art

Various methods for measurements of semiconductor surface and semiconductor/insulator interface parameters have been described. They can be classified into destructive and non-destructive. Examples of destructive methods are the secondary ion mass spectrometry and the four-point sensor method.

Non-destructive methods can be further classified into those requiring post-processing and those that don't (post-processing is defined as additional processing steps beyond those that define properties of semiconductor surface or semiconductor insulator interface that are the goal of characterization). An example of a method that requires post-processing are traditional Metal-Insulator-Semiconductor Volt-Farad (MIS CV) measurements. They require presence of an insulator over the semiconductor surface and deposition of a metal layer over the insulator. Additional steps are costly, time-consuming and they can change the properties that were the goal of measurements.

Methods that do not require post-processing can be subdivided into contact and non-contact methods. Contact methods are defined as those that involve bringing the specimen into physical contact with materials or chemicals other than the ambient environment or materials and equipment that are used to handle specimens (semiconductor wafers) during normal processing steps, such as cleaning, annealing, implantation, etc. An example of such methods in the area of semiconductor surface/interface characterization is a Mercury Sensor. Since such methods require direct contact of a foreign material with the front side of the wafer there is a risk of contaminating the wafer, therefore they are not used with production wafers.

Finally, several non-contact methods for semiconductor surface/interface characterization are known in the field.

The apparatus described in U.S. Pat. No. 5,233,291 uses traditional CV methodology for measurement of the properties of semiconductor surface and semiconductor/insulator interface. The difference between the apparatus in U.S. Pat. No. 5,233,291 and MIS CV measurement systems is in the use of precisely controlled air gap as the insulating layer between the metal electrode and the semiconductor. Wafer proximity is determined by detecting the energy losses of the laser beam that undergoes total internal reflection on the surface of the transparent conductive electrode caused by interaction of the sample with the evanescent beam. The electrode is suspended at submicron distance from the sample, this distance as well as tip and tilt being monitored by three capacitive sensors and controlled by three piezo actuators in real time during the measurements.

In order to calculate semiconductor parameters using CV methods, it is necessary to know the width of the depletion layer in the semiconductor, $W_d$. In the method in U.S. Pat. No. 5,233,281 $W_d$ is calculated from the capacitance of the depletion layer, which in turn is calculated from the total capacitance between the metal electrode and the semiconductor substrate.

$$C_{tot}^{-1} = C_{air}^{-1} + C_{SiO2}^{-1} + C_{si}^{-1},$$

Thus, it is important to know $C_{air}^{-1} + C_{SiO2}^{-1}$ at all times during the measurement, which means either measuring the air gap, holding it fixed with substantial precision during the measurements of electrical parameters of the sample, or being able to calculate it at all times during the measurement based on previously characterizing the behavior of the air gap.

Additionally, the method described in U.S. Pat. No. 5,233,291 is not well suited for measurements of samples with poorly passivated semiconductor/insulator interface, e.g. non-passivated wafers of epitaxially grown films, because of the presence of slow surface states which may recharge during the measurements and thus affect both the measurements of $C_{si}^{-1}$.

The surface photovoltage method described in U.S. Pat. No. 4,827,212 to E. Kamienicki, which patent is incorporated herein by reference makes use of modulated light whose wavelength corresponds to an energy greater than the band gap of the semiconductor and whose modulation frequency is greater than the reciprocal lifetime of minority carriers and whose intensity is low enough so that the modulation of the semiconductor surface potential is small compared to the surface potential. The photovoltage generated by the light is proportional to the width of the depletion region near the semiconductor surface. The photovoltage can be measured using capacitive coupling of a conductive electrode to the surface of the sample. The advantage of this method over regular CV methods is in the fact that it is not required to measure separate contributions of the insulating gap capacitance or the oxide capacitance which makes the method less complicated and less sensitive to errors in sensor positioning. However, this method is not a true non-contact method because it contacts the specimen with an insulating film.

In U.S. Pat. No. 5,453,703 to W. C. Goldfarb, which patent is incorporated herein by reference, a method and apparatus are disclosed for determining the minority carrier surface recombination lifetime constant ($t_s$) of a specimen of semiconductor material. The specimen is positioned between a pair of electrodes, the specimen being disposed on one of the electrodes and being spaced from the other electrode. A signal is provided corresponding to the capacitance between the specimen and electrode spaced from the specimen. A region of the surface of the specimen is illuminated with a beam of light of predetermined wavelengths and which is intensity modulated at a predetermined frequency and varying in intensity over a predetermined range. A fixed bias voltage $V_g$ applied between the pair of electrodes, the fixed bias voltage being of a value such that the semiconductor surface is in a state of depletion or inversion. A signal is provided representing the ac photocurrent induced at the region of the specimen illuminated by the light beam. The intensity of the light beam and frequency of modulation of the light beam are selected such that the ac photocurrent is nearly proportional to the intensity of the light beam and reciprocally proportional to the frequency of modulation of the light beam. A signal is provided corresponding to the illumination intensity of the beam of light. The surface minority carrier recombination time constant ($t_s$) is then determined using the ac photocurrent capacitance and illumination intensity information.

In a book entitled Semiconductor Material and Device Characterization, by Dieter K. Schroder, John Wiley & Sons, Inc. 1990, p. 46, there is disclosed a dopant measurement method for MOS capacitors using a deep depletion condition.

It is an object of this invention to provide a new and improved method and apparatus for characterizing a semiconductor.

It is another object of this invention to provide a new and improved method and apparatus for determining the doping concentration profile and average doping concentration of a specimen of semiconductor material.

It is another object of this invention to provide a non-contact method and apparatus for determining the doping concentration profile and average doping concentration of a specimen of semiconductor material.

It is still another object of this invention to provide a non-contact method and apparatus for determining the depletion width of a specimen of semiconductor material in which photovoltage (or photocurrent) is measured using capacitive coupling of a sensor electrode to the surface of the specimen.

It is a further object of this invention to provide a method and apparatus as described above which is particularly suitable for characterization of specimens with high density of slow surface states, e.g. non-passivated wafers.

It is still a further object of this invention to provide a new and improved sensor assembly for use in non-contact measuring of semiconductor surface photovoltage or photocurrent.

It is another object of this invention to provide a new and improved capacitive pickup type sensor assembly.

It is still another object of this invention to provide a non-contact method of measuring semiconductor surface properties.

It is another object of this invention to provide a non-contact method and apparatus for determining the depletion width of a semiconductor by measuring the capacitance of the depletion width in series with a known capacitance, rather than using light.

SUMMARY OF THE INVENTION

According to one embodiment of this invention, a non-contact method is provided for determining the doping concentration profile of a specimen of semiconductor material, the specimen having a surface arranged for illumination, the method comprising providing a pair of electrodes, positioning the specimen between the pair of electrodes, the specimen being disposed on one of the electrodes and spaced from the other electrode by a non-conducting medium, illuminating a region of the surface of the specimen arranged for illumination with a beam of light of wavelength shorter than that of the energy gap of the semiconductor, the beam of light being intensity modulated at a predetermined frequency, applying a variable DC voltage between the pair of electrodes, the variable DC bias voltage varying between that corresponding to accumulation and that corresponding to deep depletion for the specimen, the intensity of the light beam being low enough and the rate at which the DC bias voltage varies being fast enough such that no inversion layer is formed at the surface of the specimen, providing a signal representing the ac photocurrent at the region of the specimen illuminated by the light beam, the intensity of the light beam and frequency of modulation of the light beam being such that the ac photocurrent is nearly proportional to the intensity of the light beam, providing a signal corresponding to the total capacitance between the two electrodes during the DC bias voltage sweep, providing a signal corresponding to the variable DC bias voltage, and then, determining the doping concentration profile using the ac photocurrent, total capacitance and DC bias voltage information.

Instead of providing a signal representing the ac photocurrent, a signal may be provided corresponding to the ac photovoltage.

Once the doping concentration profile has been determined, the average doping concentration can be easily determined.

The apparatus of the invention includes a non-contact sensor assembly for determining the ac photocurrent of a specimen of semiconductor material, the non-contact sensor assembly including a sensor tip which is mounted on an air bearing assembly, the air bearing assembly being mounted through a bellows assembly on the bottom of a housing assembly, the bellows assembly including a bellows, the air bearing assembly being supplied air through the bellows, the sensor tip including a coating which serves as a reference electrode and a coating which serves as a guard electrode.

According to one implementation of the invention, the sensor tip includes a soft, compliant bottom protective layer to protect the sensor tip from mechanical damage that could be caused if large particles were present on the surface of the specimen.

According to another feature of the invention, a method and apparatus are provided for determining the resistivity and resistivity profile of a specimen of semiconductor material.

According to a further feature of the invention, the reference electrode is circularly shaped, the guard electrode is annularly shaped and both electrodes are disposed on the bottom surface of a transparent substrate.

According to another embodiment of this invention, a non-contact method is provided for determining the doping concentration profile of a specimen of semiconductor material, the method comprising providing a pair of electrodes, positioning the specimen between the pair of electrodes, the specimen being disposed on one of said electrodes and spaced from said other electrode by a non-conducting gaseous medium, applying a variable DC bias voltage between the pair of electrodes, the variable bias voltage varying between that corresponding to accumulation and that corresponding to depletion for the specimen, the rate at which the DC bias voltage varies being such that no inversion layer is formed at the surface of the specimen and the period of variation being small compared to the amount of time required to charge or discharge the surface states associated with an unknown surface, providing a signal corresponding to the DC bias voltage, providing a signal corresponding to the total capacitance between the two electrodes during the DC bias voltage sweep, providing information corresponding to the area of the electrode spaced from the specimen, determining the capacitance of the nonconductive gaseous medium using the total capacitance signal, determining the depletion width using the total capacitance, the capacitance of the nonconducting gaseous medium and the area of the electrode spaced from the specimen information, and determining the doping concentration profile using the depletion width, the total capacitance, the DC bias voltage, and the area of the electrode spaced from the specimen information.

Various features and advantages will appear from the description to follow. In the description, reference is made to the accompanying drawings which form a part thereof, and in which is shown by way of illustration, a specific embodiment of an apparatus for practicing the invention. This embodiment will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS

In the drawings wherein like reference numerals represent like parts:

FIG. 4 is a section view of the air bearing mounting cell shown in FIG. 3;

FIG. 5 is a top plan view of the air bearing mounting cell shown in FIG. 3;

FIG. 6 is a perspective view of the sensor tip shown in FIG. 2;

FIG. 7 is an enlarged front section view of the sensor tip shown in FIG. 2;

DETAILED DESCRIPTION OF PREFERRED EMBODIMENTS

The present invention is directed to a method and apparatus for determining the doping concentration profile of a specimen of semiconductor material. In one embodiment, the method and apparatus using an intensity modulated beam of light and a variable DC bias voltage and wherein the modulated light level is low enough and the variable DC bias voltage changes fast enough so that no inversion layer is formed at the specimen surface, i.e. the specimen reaches a non-equilibrium state of deep depletion. The present invention is also directed to a non contact, capacitive pickup type sensor assembly for making surface photovoltage measurements of a specimen of semiconductor material.

As will hereinafter become apparent, the doping concentration profile according to this invention can be determined using a capacitive pickup type sensor assembly other than as described herein. Also, the capacitive pickup type sensor assembly of this invention can be used for making surface photovoltage (or photocurrent) measurements for purposes other than determining doping concentration and for making measurements other than surface photovoltage (or photocurrent) and can be used for determining doping concentration without making surface photovoltage (or photocurrent) measurements.

Figure 1:
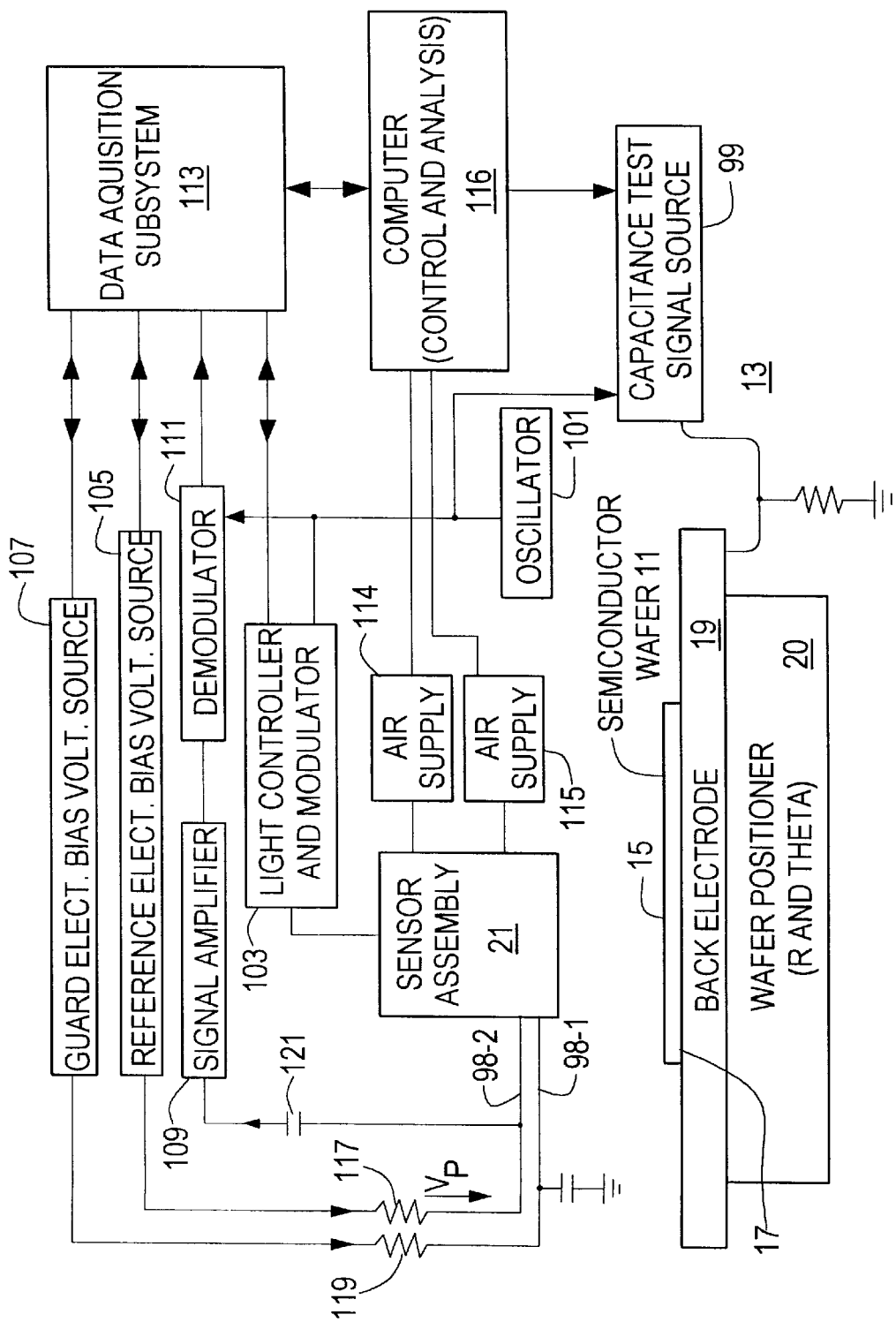
FIG. 1 is a schematic block diagram of an apparatus for practicing the invention.

Referring now to the drawings, there is shown in FIG. 1 a simplified block diagram of an apparatus for determining parameters such as the doping concentration profile of a specimen of semiconductor material according to this invention. Portions of the apparatus not pertinent to this invention are not shown. In the illustration, the specimen of semiconductor material is identified by reference numeral 11 and the apparatus of this invention is identified by reference numeral 13.

Specimen 11 has two major surfaces 15 and 17, respectively, surface 15 being the surface under testing. Specimen 11 may comprise a sample with high density of slow surface states, e.g. non passivated wafers and epitaxially grown films.

Apparatus 13 includes a back electrode 19 and a non contact capacitive pickup type sensor assembly 21. Back electrode 19 is constructed in the form of a wafer chuck and, as such, in addition to functioning as an electrode serves to support and hold specimen 11 fixed during testing. Back electrode 19 is made of a conductive metal, such as aluminum. Specimen 11 is mounted on back electrode 19 with surface 15 facing upward and surface 17 in contact with or closely spaced from back electrode 19 facing downward. Back electrode 19 is fixedly mounted on a wafer positioner 20 which is movable in R and theta directions so that different parts of the surface of specimen 11 on back electrode 19 can be positioned under sensor assembly 21 for testing.

Sensor assembly 21 is fixedly mounted vertically with respect to specimen 11.

Figure 2:
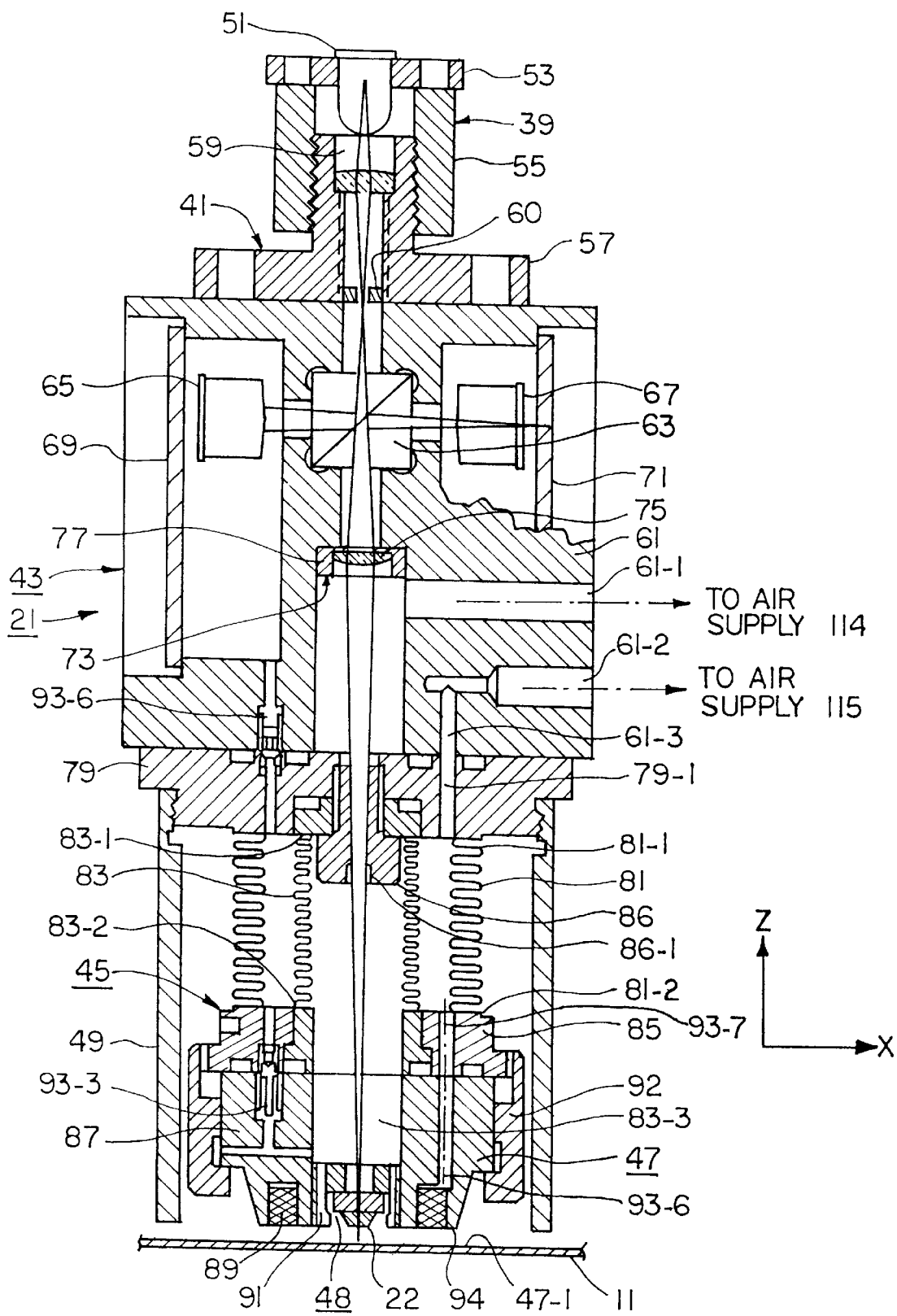
FIG. 2 is a more detailed view of the sensor assembly shown in FIG. 1.
Figure 3:
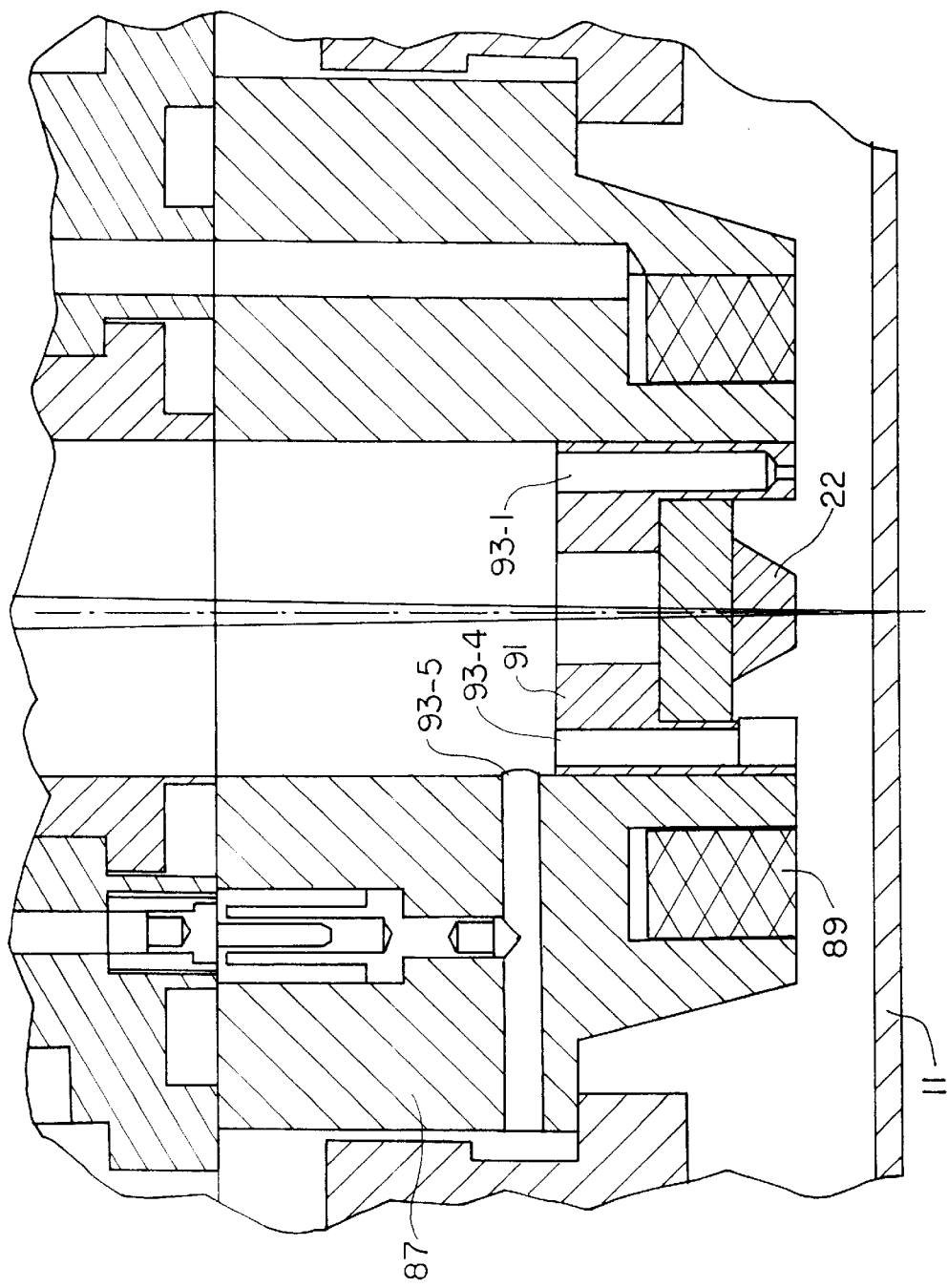
FIG. 3 is an enlarged fragmentary view of the bottom of the sensor assembly shown in FIG. 2.
Figure 9:
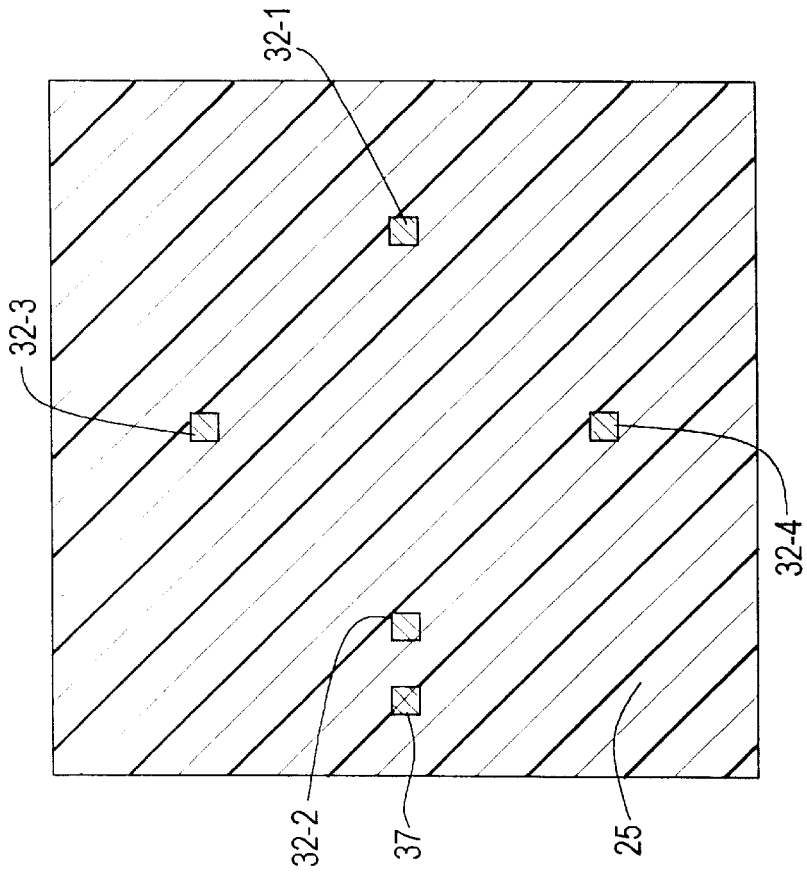
FIG. 9 is a section view taken along lines 9—9 in FIG. 7.
Figure 8:
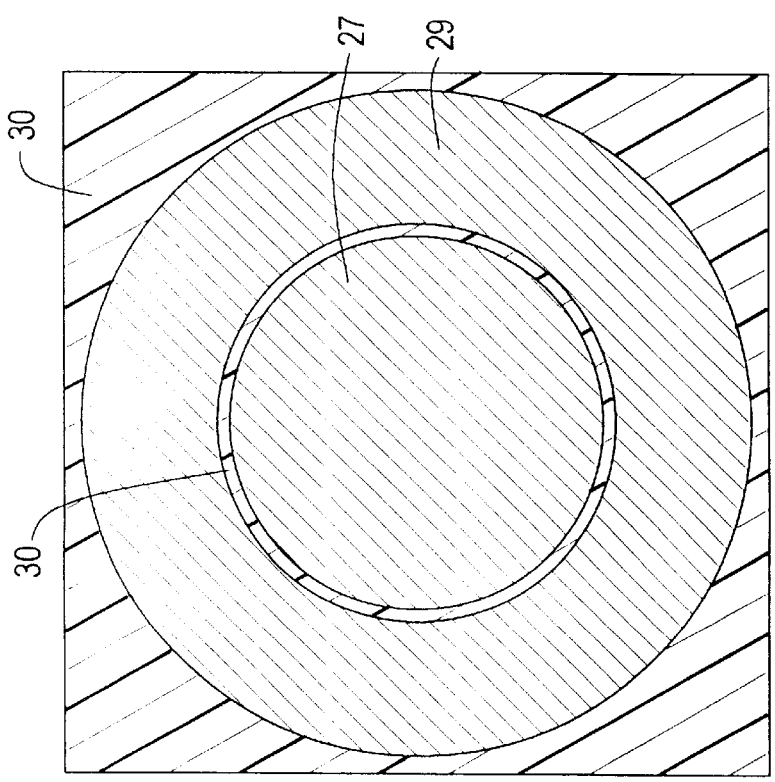
FIG. 8 is a section view taken along lines 8—8 in FIG. 7.
Figure 10:
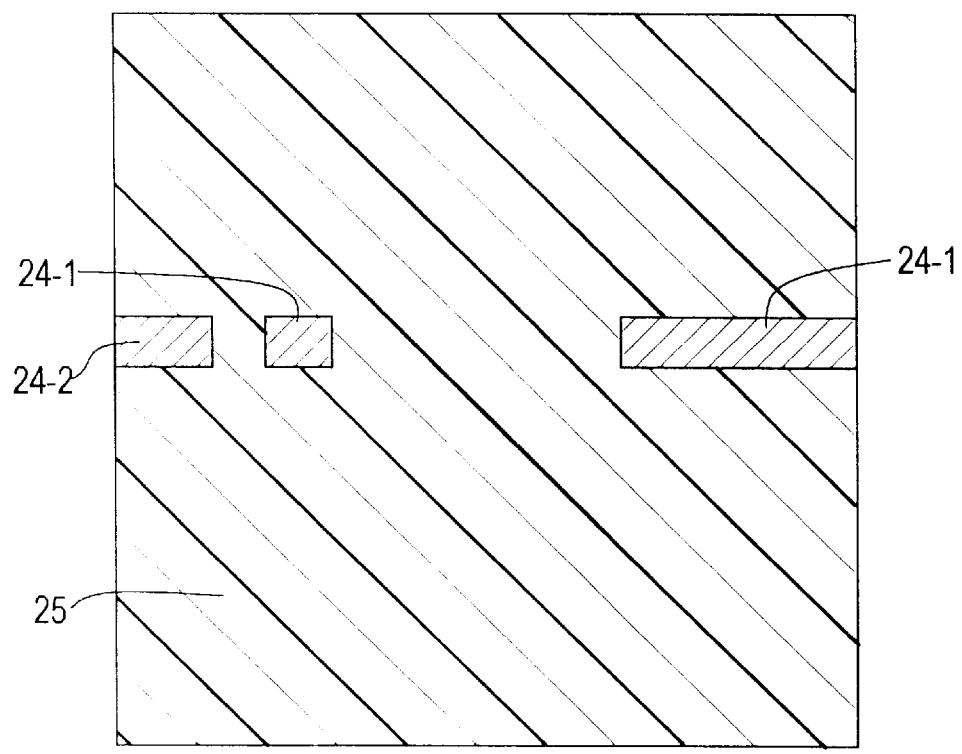
FIG. 10 is a section view taken along lines 10—10 in FIG. 7.
Figure 11:
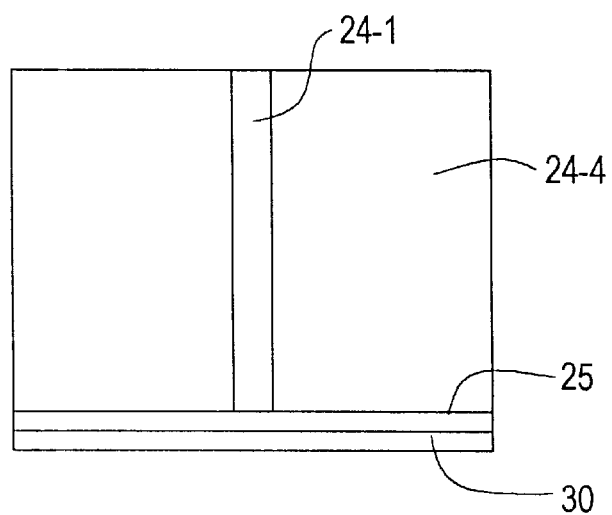
FIG. 11 is a right side view of the sensor tip shown in FIG. 7.

Sensor assembly 21 which is also shown enlarged and in more detail in FIG. 2 and further enlarged and in a fragmentary view in FIG. 3 includes a sensor tip 22.

Sensor tip 22 which is also shown in FIGS. 6 through 11 includes a truncated pyramid shaped transparent substrate 23, which may be for example quartz, the front and rear faces of substrate 23 being vertical and the side faces 24-3 and 24-4 being slanted. If desired, the front and rear faces could also be slanted, or all four faces made vertical. A pair of opaque conductive coatings 24-1 and 24-2, which may be for example titanium tungsten, are formed on substrate 23 along with a transparent insulative coating 25, such as silicon oxide. A pair of coatings 27 and 29 of conductive transparent material are formed on insulative coating 25. Coating 27 is circular in shape and serves as a reference or sensor electrode. Coating 29 is annularly shaped and serves as a guard electrode. Both coatings 27 and 29 may be made of indium-tin oxide the thickness of which determines its transparency. The thickness of coating 27 and its composition are such that it is transparent. Reference electrode 27 is smaller than specimen 11. Coating 29 is preferably, non-transparent; however, it is not essential that it be nontransparent. A soft protective transparent layer 30 which may be a plastic such as polyamide is formed underneath insulative coating 25 and electrodes 27 and 29. Coating 24-1 is electrically connected to reference electrode 27 by a quantity of conductive material 32-1 disposed in a first window 33 formed in insulative coating 25 and a quantity of conductive material 33-1 disposed in a second window 33-2 formed in coating 25. Layer 24-2 is electrically connected to guard electrode 29 by a quantity of conductive material 35 disposed in a window 37 formed in insulative coating 25 and at the other end to conductor 32-4. Conductive material 32-1 and 32-3 may be, for example indium-tin-oxide.

Referring to FIG. 2, sensor assembly 21 further includes an LED assembly 39, a condenser lens assembly 41, a housing assembly 43, a bellows assembly 45, an air bearing assembly 47, a field lens assembly 48 and a guard sleeve 49.

LED assembly 39 includes a light source in the form of an LED 51, an LED adjusting plate 53 and an LED mount 55. LED adjusting plate 53 is mounted on LED mount 55 by screws (not shown) such that it can be adjusted in the X-Y direction relative to LED mount 55 and then fixedly mounted to LED mount 55 by tightening said screws.

Condenser lens assembly 41 includes a lens mount 57 and a condenser lens 59. Condenser lens 59 is fixedly mounted on lens mount 57. Lens mount 57 includes a field stop 60.

Housing assembly 43 includes a housing 61 which is shaped to include a pair of air inlet ports 61-1 and 61-2. A 50/50 beamsplitter 63, an incident light photodiode 65, a reflected light photodiode 67, an incident light photodiode printed circuit board 69, a reflected light photodiode printed circuit board 71 and an objective lens cell assembly 73 having an objective lens 75 mounted in an objective lens holder 77 are all mounted inside housing 61.

Bellows assembly 45 includes an annular shaped upper mounting plate 79, outer and inner bellows 81 and 83, respectively, an annular shaped lower mounting plate 85 and a bellows assembly screw 86. Bellows 81 and 83 are attached at their upper ends 81-1 and 83-1 to upper mounting plate 79 and at their to lower ends 81-2 and 83-2 to mounting plate 85. Upper mounting plate 79 is fixedly mounted on the bottom of housing 61. Bellows 83 is disposed inside bellows 81. Bellows assembly screw 86 has an axial bore 86-1 for light transmission and is used to secure bellows 83 to upper mounting plate 79.

Air bearing assembly 47 includes an air bearing housing 87, a ring 89 of porous ceramic material fixedly mounted by adhesive (not shown) in housing 87 and a mounting cell 91 having orifices 93-1 through 93-8. Orifices 93-3 through 93-8 are for passage of air and orifices 93-1 and 93-2 are for passage of conductors 32-2 and 32-4. Air bearing housing 87 is secured to the bottom of lower mounting plate 85 by a Deirin nut 92. Sensor tip 22 is fixedly mounted with respect to air bearing housing 87 so that it extends out of the bottom surface 94 of bearing housing 87 and positioned so that it is underneath field lens 95 and about 0.5 micron above the specimen when in use.

Guard sleeve 49 is mounted on upper mounting plate 79 and serves to protect bellows assembly 45 and air bearing assembly 47.

Field lens assembly 48 includes a field lens 95 and a field lens mount 97.

Lead 32-2 extends up passage ways 93-4 and 93-5 to connector 93-3. Lead 32-3 (not shown) connects in a similar manner between connector 93-3 and 93-6. Lead 32-5 (not shown) connects between connector 93-6 and printed circuit board 69 where connection is made to lead 98-2 in FIG. 1. Connections are made between coating 29 and lead 98-1 of FIG. 1 in a similar manner.

Apparatus 13 further includes a capacitance test signal source 99, an oscillator 101, a light controller and modulator 103, a reference electrode bias voltage source 105, a guard electrode bias voltage source 107, a signal amplifier 109, a demodulator 111, a data acquisition system 113, a pair of high pressure air supplies 114 and 115 and a computer 116.

Capacitance test signal source 99 provides a small (i.e. a few tens of millivolts) ac potential signal on back electrode 19 so that the capacitance between wafer 11 and sensor electrode 27 can be measured. Oscillator 101 provides signals to drive LED 51 and capacitance test signal source 99. Also, oscillator 101 provides a synchronizing signal to light controller and modulator 103 and demodulator 111. Light controller and modulator 103 ac modulates and varies the amplitude of the signal provided from oscillator 101 to LED 51 so as to produce an ac modulated light beam of suitable intensity.

Reference electrode bias voltage source 105 produces a variable dc voltage whose sweep rate is controlled by computer 116. Guard electrode bias voltage source 107 produces a variable DC voltage sufficient to place an area of the surface of specimen 11 surrounding an area controlled by reference electrode 27 in accumulation during the time when the area of specimen 11 controlled reference electrode 27 is changed from accumulation to depletion.

Signal amplifier 109 amplifies the signal received from reference electrode 27. Demodulator 111, which is a synchronous demodulator, changes the ac signals received from signal amplifier 109 to dc signals. Data acquisition system 113 converts analog signals received from voltage sources 105 and 107, demodulator 111 and light controller and modulator 103 into digital signals and converts digital signals from computer 116 into analog signals. Computer 116 controls the overall operations of system 13 and processes test information received. Voltage sources 105 and 107 are connected to reference and guard electrodes 27 and 29, respectively, through separation resistors 117 and 119 respectively. Signal amplifier 109 is connected to line 31 by isolation capacitor 121.

Air supplies 114 and 115 are controlled by computer 116 and are connected to ports 61-1 and 61-2, respectively.

In using apparatus 13, specimen 11 is placed on back electrode 19 after removing back electrode 19 from under sensor assembly 21 using wafer positioner 20. Specimen 11 is then positioned under sensor assembly 21 using wafer positioner 20. Initially, air bearing assembly 47 (and sensor tip 22 which is mounted thereon) is suspended against gravity by inner and outer bellows 83 and 81 respectively, at a point approximately 2 mm above specimen 11. Bellows 83 and 81 act like extension springs, exerting an upward force on air bearing assembly 47 proportional to the distance extended. Air is then directed into housing 43 through pressure ports 61-1 and 61-2 to control the vertical position (along the Z axis) of air bearing assembly 47 (and sensor tip 22 which is mounted thereon) with respect to specimen 11. Said position control is accomplished in three phases: I) coarse approach and leveling; II) near-contact approach; and III) departure.

Coarse Approach and Leveling Phase

Air, at a pressure of approximately 40 PSIG, is first admitted to pressure port 61-1. The air is prevented from leaking upwards by lens 75 and lens cell 77, but it is conducted downward by orifice 86-1 in screw 86 into the interior space 83-3 of inner bellows 83. The pressure of the air in space 83-3 applies a downward force against sensor cell 91-1 and also causes flow down and out through orifices 93-1 through 93-6. Said force causes air bearing assembly 47 to move part-way down toward specimen 11. Additionally, air, at a pressure of approximately 8 PSIG, is admitted to pressure port 61-2 and is conducted by ports 61-3 and 79-1 into the annular space 81-1 which exists between outer bellows 81 and inner bellows 83. The pressure of the air in space 81-1 applies a downward force against end cap 85, causing air bearing assembly 47 to move farther toward specimen 11, and acting in opposition to the tension force developed by the extension of bellows 83 and 81. As air bearing assembly 47 approaches within 20–40 micrometers of specimen 11, the air flowing out through orifices 93-1 through 93-6 creates pressurized air film 47-1, opposing further downward motion of air bearing assembly 47 and creating a condition of force equilibrium such that air bearing assembly 47 floats at a stable height of approximately 20 micrometers above specimen 11. The presence of multiple identical orifices 93-1 through 93-6 ensures that air bearing assembly 47 floats parallel to specimen 11, even if air bearing assembly 47 was not perfectly parallel to specimen 11 at the initial 2 mm height. The pressure of the air in space 81-1 also forces flow through port 94 and thence through porous ring 89; however, the porosity of said porous ring is so low that said flow is negligible compared to the flow previously mentioned out of orifices 93-1 through 93-6.

At the conclusion of this approach and leveling phase, the gap between air bearing assembly 47 and specimen 11 is approximately 20 micrometers, and positioner 20 may be exercised to adjust the horizontal (X-Y) position of specimen 11 with respect to sensor tip 22.

Near-Contact Approach Phase

After equilibrium has been achieved in the coarse approach and leveling phase, the pressure of the air admitted to pressure port 61-2 is increased to approximately 25 PSIG. The increased pressure of the air in space 81-1 applies additional downward force against endcap 85, causing air bearing assembly 47 to descend further toward specimen 11. Said increased pressure also causes increased flow through porous right 89, which increases the pressure in air film 47-1 as said air film approaches 2–4 micrometers in thickness. Then the pressure of the air admitted to pressure port 61-1 is decreased to approximately atmospheric pressure. As the flow through orifices 93-1 through 93-6 subsides, air bearing assembly 47 descends to a final height of approximately 2 micrometers above specimen 11, supported on air film 47-1, which is now maintained by the flow through porous ring 89. The stiffness of air film 47-1 under said conditions is sufficient to maintain the 2 micrometer height of air bearing 47 above specimen 11, even in the presence of electrostatic forces between sensor tip 22 and specimen 11, within plus or minus approximately 0.1 micrometer. At the conclusion of this near-contact approach phase, the gap between air bearing assembly 47 and specimen 11 is approximately 2 micrometers, and measurements of specimen 11 using sensor tip 22 can be accomplished.

Departure Phase

To initiate the departure phase, the pressure of the air admitted to port 61-1 is increased to approximately 40 PSIG. As detailed above, this results in an outflow through orifices 93-1 through 93-6, which in turn causes the pressure in air film 47-1 to increase, thereby increasing the height of air bearing assembly 47 above specimen 11. Then the pressure of the air admitted to pressure port 61-2 is decreased to approximately 8 PSIG. The decreased pressure of the air in space 81-1 reduces the downward force against endcap 85, causing air bearing assembly 47 to rise further away from specimen 11 due to the tension in bellows 83 and 81. Equilibrium is achieved when air film 47-1 is approximately 20 micrometers thick. At this point, further adjustments to the horizontal (X_Y) position of specimen 11 with respect to sensor tip 22 may be carried out using positioner 20, if desired. Then the near-contact approach phase described above may be repeated. Alternatively, he departure phase can continue as follows.

The pressure of the air admitted to pressure port 61-2 is decreased to atmospheric. With the resulting decreased pressure of the air in space 81-1, the tension in bellows 83 and 81 pulls air bearing assembly 47 further away from specimen 11. Finally, the pressure of the air admitted to pressure port 61-1 is also decreased to atmospheric, and the tension in bellows 83 and 81 pulls air bearing assembly 47 up to its initial equilibrium position at approximately 2 mm above specimen 11. Sensor assembly 21 is then positioned above specimen 11.

As can be appreciated, air from supplies 114 and 115 serves two purposes, namely (1) form an air bearing for sensor assembly 21 and (2) cause bellows 81 and 83 to expand in order to lower sensor assembly 21 into the desired position for testing.

Led 51 which is ac intensity modulated and controlled by light controller and modulator 103 as instructed by computer 115 is focused by lens 59 on stop 60. Light emerging from stop 60 and reflected by beamsplitter 63 strikes photodiode 65. Light transmitted through beamsplitter 63 from stop 60 passes through objective lens 75, through field lens 95, through sensor tip 22 and strikes specimen 11 to generate ac photovoltage. The light reflected from specimen 11 passes back through field lens 95 and objective lens 75 and is then split 50/50, so that 50% of it is detected by photodiode 67. The signal from photodiode 67 is fed by wire 122 to data acquisition subsystem 113 through an amplified signal path in signal amplifiers 109 (not shown) into PCB 71 which is coupled to computer 116 by a wire (not shown). Light from stop 60 that is reflected off beamsplitter 63 strikes incident light photodiode 65. The signal from incident light photodiode 65 is fed by a wire 123 to data acquisition system 113 through an amplified signal path in signal amplifiers 109. The difference in intensity of the light striking specimen 11, which is the same with suitable anti-reflective coatings applied to air-dielectric interfaces. The difference in intensity of the light striking specimen 11, which is the same with suitable anti-reflective coatings applied to air-dielectric interfaces as the intensity of the light from stop 60 that is reflected off beamsplitter 63 into photodiode 65 since beamsplitter 63 splits in half the light from stop 60, and the light reflected from specimen 11 is equal to the light absorbed by specimen 11 (i.e. absorbed flux is equal to incident flux minus reflected flux). With specimen 11 so illuminated and absorbed flux so measured time-varying bias voltages from sources 105 and 107, controlled by computer 51, are applied to their respective electrodes 27 and 29 through separation resistors 117 and 119, respectively.

The ac photovoltage signal developed on the surface 15 of specimen 11 upon illumination, which is of one frequency, and the ac capacitance test signal from source 99 which is of a frequency different from the ac photovoltage signals are capacitively picked up simultaneously by reference electrode 27 and fed through an isolation capacitor 121 into signal amplifier 109 where they are separated into different channels using conventional electrical filter circuits. Signals picked up by guard electrode 29 are shunted to ground. As can be appreciated, guard electrode 29 also serves to avoid fringing field problems in the application of the bias field by the reference electrode and also serves to limit the area on surface 15 of specimen 11 that provides the ac surface photovoltage signal to reference electrode 27. The output of signal amplifier 109 is fed into demodulator 111. The output of demodulator 111 is fed into data acquisition system 113 whose output is fed into computer 115.

A method of determining the doping concentration profile $N_{sc}$ (Z) according to this invention and using apparatus 13 will now be described.

Figure 12:
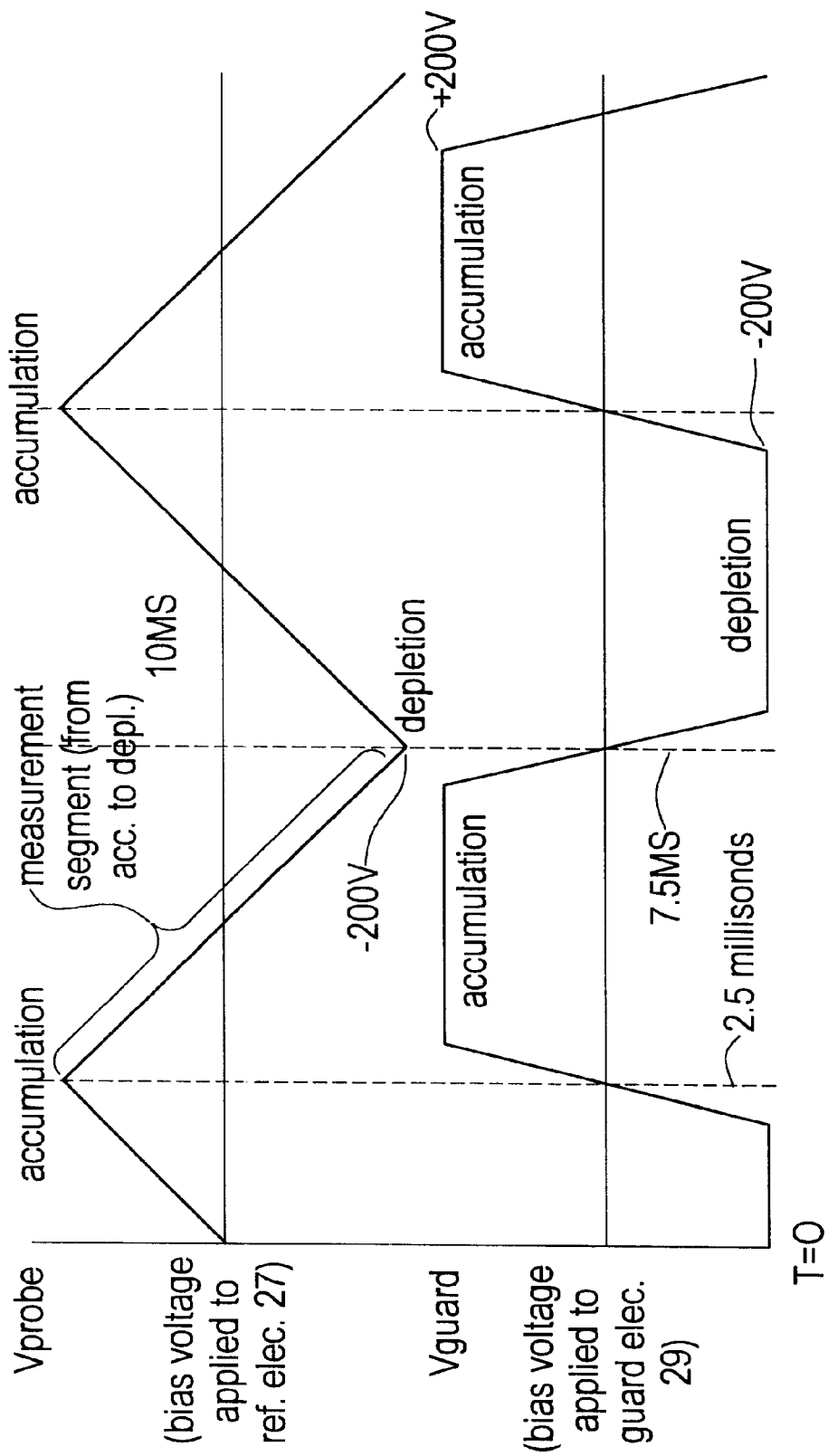
FIG. 12 is a graph showing how the sensor voltage and guard voltage vary in time as measurements of doping concentration are being made according to this invention.

The first step involves determining the value of the induced charge $Q_{ind}$ at a plurality of points in time during the measurement segment of the sweep period, the measurement segment being the time period when the voltage applied to reference electrode 27 varies from that corresponding to accumulation to that corresponding to deep depletion as shown in FIG. 12. The induced charge $Q_{ind}$ is determined using the formula:

$$Q_{ind} = C_{tot} \cdot V_p$$

where:

$C_{tot}$=total capacitance between the pair of electrodes 19 and 27, and $V_p$=sensor potential (i.e. the bias voltage applied between electrodes 19 and 27).

Then, Wd is determined for the same plurality of points in time using the formula:

$$I_{ac} = |e|/\epsilon_{si} \cdot C_{tot} \cdot W_d \cdot \phi,$$

where:

$W_d$=the depletion layer width,
e=electron charge,
$\epsilon_{si}$=dielectric constant of Si,
$C_{tot}$=total capacitance between the pair of electrodes,
$\phi$=absorbed flux (photons/cm²·s) where s=seconds and
$I_{ac}$=current induced in the reference electrode by the ac surface photovoltage.

Then, the doping concentration profile is determined using the formula:

$$N_{SC}(Z) = (-1/eA) \cdot (dQ_{ind}/dW_d)$$

where:

$N_{SC}$ (Z) the doping concentration at a depth Z,
A=the sensor area, and
Z=$W_d$ Once $N_{SC}$ (Z) has been determined, the resistivity can be determined using well known computations. For example, for boron-doped silicon the resistivity can be determined using a commonly accepted formula such as:

$$\rho = (6.242 \times 10^{13}/N_{SC}) \cdot 10^t$$

where:

$$t = (A_0 + A_1 \cdot Y + A_2 \cdot Y^2 + A_3 \cdot Y^3)/(1 + B_1 \cdot Y + B_2 \cdot Y^2 + B_3 \cdot Y^3)$$

where:

$y = (\log_{10} N_{sc}) - 16$, $\quad A_3 = 0.057501$, $A_0 = -3.0769$, $\quad B_1 = -0.68157$, $A_1 = 2.2108$, $\quad B_2 = 0.19833$, and $A_2 = -0.62272$, $\quad B_3 = -0.018376$ Referring now to FIG. 12 there is shown a graph of an example how the bias voltage applied to reference electrode 27 and guard electrode 29 may vary for the following conditions, the conditions being selected for illustrative purposes only:

| | |
|---|---|
| LED modulation frequency | 100 kHz; |
| Bias sweep period | 10 ms; |
| Maximum bias voltage | 200 V; |
| Incident flux | $10^{13}$ photons/cm²/s. |

Instead of air, another nonconductive gas could be used such as dry nitrogen. Similarly, a non-conducting, non-gaseous medium, such as mylar, could be used in an implementation of the invention which contacts the wafer.

In a situation where the amount of optically generated minority carriers (optically injected charge) is small enough not to create an inversion layer, but not small enough negligible compared to the charge in the depletion region, the following method can be used to correct for the optically injected charge.

$$Q_{ind} = -(Q_{sc} + Q_{inj}) \tag{1}$$

$$Q_{ind} = C_{tot} \cdot V_{probe}, \tag{2}$$

$$Q_{sc} = eA \int N_{sc}(Z) dz, \tag{3}$$

$$Q_{inj} = eA \cdot \phi \cdot t, \tag{4}$$

where $\phi$ is the optical flux and t is time from the start of the depletion part of the sweep.

$Q_{ind}$ and $Q_{inj}$ are found from measurements and equations (2) and (4); $Q_{SC}$ is found from (1), and then the doping profile $N_{SC}(Z)$ is found from (3).

Instead of using photovoltage (or photocurrent), the depletion width can be measured according to another embodiment of this invention by measuring the capacitance of the depletion width and by calculating the depletion width from the capacitance. The method is as follows:

a. providing a pair of electrodes, b. positioning the specimen between the pair of electrodes, the specimen being disposed on one of said electrodes and spaced from said other electrode by a nonconducting gaseous medium, c. applying a variable DC bias voltage between the pair of electrodes, the variable bias voltage varying between that corresponding to accumulation and that corresponding to depletion for the specimen, d. the rate at which the DC bias voltage varies being such that no inversion layer is formed at the surface of the specimen and the period of variation being small compared to the amount of time required to charge or discharge the surface states associated with an unknown surface, e. providing a signal corresponding to the DC bias voltage, f. providing a signal corresponding to the total capacitance between the two electrodes during the DC bias voltage sweep, g. providing information corresponding to the area of the electrode spaced from the specimen, h. determining the capacitance of the nonconductive gaseous medium using the total capacitance signal, i. determining the depletion width using the total capacitance, the capacitance of the nonconducting gaseous medium and the area of the electrode spaced from the specimen information, and j. determining the doping concentration profile using the depletion width, the total capacitance, the DC bias voltage, and the area of the electrode spaced from the specimen information, wherein determining the capacitance of the nonconductive gaseous medium comprises measuring the total capacitance between the two electrodes when the DC bias voltage corresponds to that for accumulation for the specimen and wherein the depletion width is determined using the formula $W_d = \epsilon_s \epsilon_o A [(1/C_{tot}) - (1/C_{ngm})]$ where:
$W_d$ = the depletion layer width,
$\upsilon_s$ = the relative dielectric constant of the semiconductor,
$\upsilon_o$ = the absolute dielectric constant of a vacuum,
A = the area of the electrode spaced from the specimen,
$C_{tot}$ = the total capacitance between the pair of electrodes, and
$C_{ngm}$ = the capacitance of the nonconducting gaseous medium.

Once the depletion width is determined, the doping concentration profile is determined using the formula $N(W_d) = C^3_{tot} / q \epsilon_s \epsilon_o A^2 (dC_{tot}/dV)$ where:
N = the doping concentration,
W = the depletion layer width,
$C_{tot}$ = the total capacitance between the pair of electrodes,
q = the elementary charge
$\epsilon_s$ = the relative dielectric constant of the specimen,
$\epsilon_o$ = the absolute dielectric constant of a vacuum,
A = the area of the electrode spaced from the specimen, and
V = the applied DC bias voltage.

The apparatus used in determining doping concentration by measuring capacitance as described above can be apparatus 13 as shown in FIG. 1 with light source 51 not being energized. Also, non-contact sensor assembly other than the air-bearing arrangement shown by FIG. 2 could also be employed in either embodiment of the method of this invention.

The embodiments of the present invention are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A non-contact method of determining the doping concentration profile of a specimen of semiconductor material, the specimen having a surface arranged for illumination, the method comprising:

a. providing a pair of electrodes,
    b. positioning the specimen between the pair of electrodes, said specimen being disposed on one of said electrodes and spaced from said other electrode by a nonconducting medium,
    c. illuminating a region of the surface of the specimen arranged for illumination with a beam of light of wavelength shorter than that of the energy gap of the semiconductor, the beam of light being intensity modulated at a predetermined frequency,
    d. applying a variable DC bias voltage between the pair of electrodes, the variable bias voltage varying between that corresponding to accumulation and that corresponding to depletion for the specimen,
    e. the intensity of the light beam and the rate at which the DC bias voltage varies being such that no inversion layer is formed at the surface of the specimen,
    f. providing a signal corresponding to the total capacitance between the two electrodes during the DC voltage sweep,
    g. providing a signal representing the ac photovoltage at the region of the specimen illuminated by the light beam,
    h. the intensity of the light beam and frequency of modulation of the light beam being such that the ac photovoltage is nearly proportional to the intensity of the light beam,
    i. providing a signal corresponding to the variable DC bias voltage, and then
    j. determining the doping concentration profile using said ac photovoltage, total capacitance and DC bias voltage information.

2. The method of claim 1 wherein said nonconducting medium is a gas.

3. The method of claim 2 wherein said gas is air.

4. The method of claim 2 wherein said gas is nitrogen or $SF_6$.

5. The method of claim 1 wherein determining the doping concentration profile comprises:

a. determining the value of the induced charge $Q_{ind}$ at a plurality of points during a segment of the DC bias voltage sweep period,
    b. determining the depletion width $W_d$ at said plurality of points, and
    c. determining the doping concentration profile $N_{SC}(Z)$ using $Q_{ind}$ and $W_d$.

6. The method of claim 5 where $Q_{ind}$ is determined using the formula $Q_{ind} = C_{tot} \cdot V_p$ where $C_{tot}$ = the total capacitance between the pair of electrodes and $V_p$ = the sensor potential.

7. The method of claim 6 where $W_d$ is determined using the formula:

$$I_{ac} = |e|/\epsilon_{si} \cdot C_{tot} \cdot W_d \cdot \phi_1;$$

where:
$W_d$ = the depletion layer width,
e = electron charge,
$\epsilon_{si}$ = dielectric constant of Si,
$C_{tot}$ = total capacitance between the pair of electrodes,
$\phi$ = absorbed flux (photons/cm$^2 \cdot$s) where s = seconds and
$I_{ac}$ = current induced in a reference electrode by the ac surface photovoltage.

8. A method of determining the resistivity of a specimen of semiconductor material, the specimen having a surface arranged for illumination, the method comprising:

a. providing a pair of electrodes,
    b. positioning the specimen between the pair of electrodes, said specimen being disposed on one of said electrodes and spaced from said other electrode by a nonconducting medium,
    c. providing a signal corresponding to the total capacitance between the two electrodes,
    d. illuminating a region of the surface of the specimen arranged for illumination with a beam of light of wavelengths shorter than that of the energy gap of the semiconductor, the beam of light being intensity modulated at a predetermined frequency,
    e. applying a variable DC bias voltage ($V_g$) between the pair of electrodes, the variable bias voltage varying between that corresponding to accumulation and that corresponding to depletion for the specimen, f. the intensity of the light beam and the rate at which the DC bias voltage varies being such that no inversion layer is formed at the surface of the specimen, g. providing a signal representing the ac photovoltage at the region of the specimen illuminated by the light beam, h. the intensity of the light beam and frequency of modulation of the light beam being such that the ac photovoltage is nearly proportional to the intensity of the light beam, i. providing a signal corresponding to the bias voltage ($V_g$), j. determining the doping concentration ($N_{sc}$) profile using said ac photovoltage, total capacitance and DC bias voltage information, and k. determining the resistivity using the doping concentration.

9. The method of claim 8 wherein determining the doping concentration profile includes determining the depletion layer width using the formula:

$$I_{ac}=|e|/E_{si} \cdot C_{tot} \cdot W_d \cdot \Phi,$$

where:
$W_d$=the depletion layer width,
e=electron charge,
$\epsilon_{si}$=dielectric constant of Si,
$C_{tot}$=total capacitance between the pair of electrodes,
$\Phi$=absorbed flux (photons/cm$^2$·s) where s=seconds and
$I_{ac}$=current induced in a reference electrode by the ac surface photovoltage.

10. The method of claim 9 wherein the doping concentration profile is determined using the formula:

$$N(z)=(1/|e|A) \cdot (dQ_{ind}/dW_d);$$

where, $z=W_d.$

11. A method of determining the resistivity of a specimen of semiconductor material, the specimen having a surface arranged for illumination, the method comprising:

a. providing a pair of electrodes, b. positioning the specimen between the pair of electrodes, said specimen being disposed on one of said electrodes and spaced from said other electrode by a nonconducting medium, c. providing a signal corresponding to the total capacitance between the two electrodes, d. illuminating a region of the surface of the specimen arranged for illumination with a beam of light of wavelengths shorter than that of the energy gap of the semiconductor, the beam of light being intensity modulated at a predetermined frequency, e. applying a variable DC bias voltage ($V_g$) between the pair of electrodes, the variable bias voltage varying between that corresponding to accumulation and that corresponding to depletion for the specimen, f. the intensity of the light beam and the rate at which the DC bias voltage varies being such that no inversion layer is formed at the surface of the specimen, g. providing a signal representing the ac photocurrent at the region of the specimen illuminated by the light beam, h. the intensity of the light beam and frequency of modulation of the light beam being such that the ac photovoltage is nearly proportional to the intensity of the light beam, i. providing a signal corresponding to the bias voltage ($V_g$), j. determining the doping concentration ($N_{sc}$) profile using said ac photocurrent, total capacitance and DC bias voltage information, and k. determining the resistivity using the doping concentration.

12. The method of claim 11 wherein the specimen is boron-doped silicon and the resistivity $\rho$ is determined using the formula:

$$\rho=(6.242\times10^{13}/N_{sc}) \cdot 10^{\,t}$$

$$t=(A_0+A_1 \cdot Y+A_2 \cdot Y^2+A_3 \cdot Y^3)/(1+B_1 \cdot Y+B_2 \cdot Y^2+B_3 \cdot Y^3).$$

13. A non-contact sensor assembly for making ac surface photocurrent measurements of a specimen of semiconductor material when illuminated by light comprising:

a. a housing having a top and a bottom, b. a bellows assembly, said bellows assembly comprising an upper plate, a lower plate and a bellows connecting the upper plate to the lower plate, said upper plate being mounted on said bottom of said housing, c. an air bearing assembly mounted on said bottom plate of said bellow assembly, and d. a sensor tip mounted on said air bearing assembly, said sensor tip including an electrode, e. said housing having an inlet for receiving air from an air supply and direct said air into said air bearing through said bellows.

14. A non-contact capacitive pickup type sensor assembly comprising:

a. a housing, b. a bellows assembly mounted on said housing, said bellows assembly including a first bellows, c. an air bearing assembly mounted on said bellow assembly, and d. a sensor tip mounted on said air bearing assembly, said sensor tip including an electrode, e. said housing having an inlet for receiving air from a first air supply and directing said air into said air bearing assembly through said bellows, said air passing through said bellows causing said bellows to expand.

15. The sensor assembly of claim 14 wherein said air bearing assembly includes a plurality of orifices and wherein said air from said first bellows exits through said orifices.

16. The sensor assembly of claim 15 wherein said bellows assembly includes a second bellows and wherein said housing includes an inlet for receiving air from a second air supply and directing air into said air bearing through said second bellows.

17. The sensor assembly of claim 16 wherein said bearing assembly includes a porous ring and said air from said second bellows exits said air bearing through said porous ring.

18. The sensor assembly of claim 17 and further including a light source and wherein said first bellows is an outer bellows and said second bellows is an inner bellows.

19. The sensor assembly of claim 18 wherein said sensor tip including a substrate having a coating serving as a reference electrode.

20. The sensor assembly of claim 19 wherein said sensor tip further includes a coating serving as a guard electrode.

21. The sensor assembly of claim 20 wherein said sensor tip further includes a soft protective layer.

22. The sensor assembly of claim 21 wherein said soft protective layer is a plastic.

23. The sensor assembly of claim 22 wherein said plastic is a polyamide or parylene.

24. A method of determining the doping concentration profile of a specimen of semiconductor material, the method comprising:
   a. providing a pair of electrodes,
   b. positioning the specimen between the pair of electrodes, the specimen being disposed on one of said electrodes and spaced from said other electrode by a nonconducting medium,
   c. applying a variable DC bias voltage between the pair of electrodes, the variable bias voltage varying between that corresponding to accumulation and that corresponding to depletion for the specimen,
   d. the rate at which the DC bias voltage varies being such that no inversion layer is formed at the surface of the specimen and the period of variation being small compared to the amount of time required to charge or discharge the surface states associated with an unknown surface,
   e. providing a signal corresponding to the DC bias voltage,
   f. providing a signal corresponding to the total capacitance between the two electrodes during the DC bias voltage sweep,
   g. providing information corresponding to the area of the electrode spaced from the specimen,
   h. determining the capacitance of the nonconductive medium using the total capacitance signal,
   i. determining the depletion width using the total capacitance, the capacitance of the nonconductive medium and the area of the electrode spaced from the specimen information, and
   j. determining the doping concentration profile using the depletion width, the total capacitance, the DC bias voltage, and the area of the electrode spaced from the specimen information.

25. The method of claim 24, wherein determining the capacitance of the nonconductive gaseous medium comprises measuring the total capacitance between the two electrodes when the DC bias voltage corresponds to that for accumulation for the specimen.

26. The method of claim 24 wherein the depletion width is determined using the formula:

$$W_d \epsilon_s E_o A[(1C_{tot})-(1/C_{nm})]$$

where:
   $W_d$=the depletion layer width,
   $\epsilon_s$=the relative dielectric constant of the semiconductor,
   $\epsilon_o$=the absolute dielectric constant of a vacuum,
   A=the area of the electrode spaced from the specimen,
   $C_{tot}$=the total capacitance between the pair of electrodes, and
   $C_{nm}$=the capacitance of the nonconducting medium.

27. The method of claim 26 wherein the doping concentration profile is determined using the formula:

$$N(W_d)=C^3_{tot}/q\epsilon_s\epsilon_o A^2(dC_{tot}/dV)$$

where:
   N=the doping concentration,
   W=the depletion layer width,
   $C_{tot}$=the total capacitance between the pair of electrodes,
   q=the elementary charge
   $\epsilon_s$=the relative dielectric constant of the specimen,
   $\epsilon_s$=the absolute dielectric constant of a vacuum,
   A=the area of the electrode spaced from the specimen, and
   V=the applied DC bias voltage.

28. The method of claim 24, wherein the nonconductive medium is air.

29. The method of claim 7, wherein the doping concentration profile is determined using the formula:

$$N_{sc}(Z)=(-1/eA)\cdot(dQ_{ind}/dW_d)$$

where:
   $N_{sc}$ (Z) the doping concentration at a depth Z,
   A=the sensor area, and
   $Z=W_d$.

30. A method of determining properties of a specimen of semiconductor material, the specimen having a surface arranged for illumination, the method comprising:
   a. providing a pair of electrodes,
   b. positioning the specimen between the pair of electrodes, said specimen being disposed on one of said electrodes and spaced from said other electrode by a nonconducting medium,
   c. illuminating a region of the surface of the specimen arranged for illumination with a beam of light of wavelength shorter than that of the energy gap of the semiconductor, the beam of light being intensity modulated at a predetermined frequency,
   d. applying a variable DC bias voltage between the pair of electrodes, the variable bias voltage varying between that corresponding to accumulation and that corresponding to depletion for the specimen,
   e. the intensity of the light beam and the rate at which the DC bias voltage varies being such that no inversion layer is formed at the surface of the specimen,
   f. providing a signal corresponding to the total capacitance between the two electrodes during the DC voltage sweep,
   g. providing a signal representing the ac photovoltage at the region of the specimen illuminated by the light beam,
   h. the intensity of the light beam and frequency of modulation of the light beam being such that the ac photovoltage is nearly proportional to the intensity of the light beam,
   i. providing a signal corresponding to the variable DC bias voltage, and then
   j. determining properties of said specimen of semiconductor material using said ac photovoltage, total capacitance and DC bias voltage information.

31. A non-contact method of determining properties of a specimen of semiconductor material, the specimen having a surface arranged for illumination, the method comprising:

a. providing a pair of electrodes,
b. positioning the specimen between the pair of electrodes, said specimen being disposed on one of said electrodes and spaced from said other electrode by a nonconducting medium,
c. illuminating a region of the surface of the specimen arranged for illumination with a beam of light of wavelength shorter than that of the energy gap of the semiconductor, the beam of light being intensity modulated at a predetermined frequency,
d. applying a variable DC bias voltage between the pair of electrodes, the variable bias voltage varying between that corresponding to accumulation and that corresponding to depletion for the specimen,
e. providing a signal corresponding to the total capacitance between the two electrodes during the DC voltage sweep,
f. providing a signal representing the ac photovoltage at the region of the specimen illuminated by the light beam,
g. the intensity of the light beam and frequency of modulation of the light beam being such that the ac photovoltage is nearly proportional to the intensity of the light beam,
h. providing a signal corresponding to the variable DC bias voltage, and then
i. determining properties of said specimen of semiconductor material using said ac photovoltage total capacitance and DC bias voltage information.

32. The method of claim 31 wherein said other electrode is spaced from said one electrode through an air bearing.

33. The method of claim 24, wherein the nonconductive medium is a gas.

* * * * *